(12) United States Patent
Son et al.

(10) Patent No.: US 6,720,573 B2
(45) Date of Patent: Apr. 13, 2004

(54) ELECTRONIC DEVICE COMPRISING ORGANIC COMPOUND HAVING P-TYPE SEMICONDUCTING CHARACTERISTICS

(75) Inventors: Se-Hwan Son, Taejeon (KR); Ok-Hee Kim, Taejeon (KR); Seok-Hee Yoon, Taejeon (KR); Kong-Kyeom Kim, Taejeon (KR); Youn-Gu Lee, Seoul (KR); Jae-Soon Bae, Taejeon (KR)

(73) Assignee: LG Chemical Co., Ltd., Seoul (KR)

( * ) Notice: Subject to any disclaimer, the term of this patent is extended or adjusted under 35 U.S.C. 154(b) by 0 days.

(21) Appl. No.: 09/914,731

(22) PCT Filed: Dec. 27, 2000

(86) PCT No.: PCT/KR00/01537

§ 371 (c)(1),
(2), (4) Date: Aug. 30, 2001

(87) PCT Pub. No.: WO01/49806

PCT Pub. Date: Jul. 12, 2001

(65) Prior Publication Data

US 2002/0158242 A1 Oct. 31, 2002

(30) Foreign Application Priority Data

Dec. 31, 1999 (KR) ......................................... 1999-67746
Dec. 26, 2000 (KR) ......................................... 2000-82085

(51) Int. Cl.$^7$ ......................... H01L 35/24; H01L 51/00
(52) U.S. Cl. ..................................... 257/40; 428/411.1
(58) Field of Search ........................ 428/411.1; 257/40

(56) References Cited

U.S. PATENT DOCUMENTS

| 4,356,429 | A | 10/1982 | Tang ........................... 313/503 |
| 4,780,536 | A | 10/1988 | Czarnik et al. ............. 544/225 |
| 5,366,811 | A | 11/1994 | Higashi et al. ............. 428/457 |
| 5,540,999 | A | 7/1996 | Yamamoto et al. ...... 428/411.1 |
| 5,616,427 | A | 4/1997 | Tada ........................... 428/690 |
| 6,312,838 | B1 | * 11/2001 | Ishibashi et al. ............. 428/690 |
| 6,436,559 | B1 | 8/2002 | Ueno et al. ................. 428/690 |

FOREIGN PATENT DOCUMENTS

| JP | 06-163158 | 6/1994 |
| JP | 07-11249 | 1/1995 |

OTHER PUBLICATIONS

Kruger, Jessica, et al., "Modification of $TiO_2$ Heterojunctions with Benzoic Acid Derivatives in Hybrid Molecular Solid–State Devices," *Advanced Materials*, vol. 12, pp. 447–451 (2000).

Kim, J.S., et al., "Indium–tin oxide treatments for single- and double–layer polymeric light–emitting diodes: The relation between the anode physical, chemical, and morphological properties and the device performance," *Journ. of Applied Physics*, vol. 84, No. 12, pp. 6858–6870 (Dec. 15, 1998).

Pieterse, Koen, et al., "Towards Organic N–Type Semi-Conducting Materials," *Polymer Preprint*, 40, pp. 404–405 (1999).

* cited by examiner

Primary Examiner—George Eckert
Assistant Examiner—Joseph Nguyen
(74) Attorney, Agent, or Firm—Ladas & Parry

(57) ABSTRACT

The present invention relates to electronic devices comprising an organic compound acting to inject or transport holes with p-type semi-conducting characteristics. The present invention provides for electronic devices comprising at least one or more layers selected from a group composed of a hole injecting layer, a hole transporting layer, and a hole injecting and transporting layer which comprises hexaazatriphenylene based organic compound represented by chemical formula (1), wherein the devices can use low drive-voltage, and can improve a light-emitting life.

31 Claims, 2 Drawing Sheets

ELECTRONIC DEVICE COMPRISING ORGANIC COMPOUND HAVING P-TYPE SEMICONDUCTING CHARACTERISTICS

CROSS REFERENCE TO RELATED APPLICATION

This application is based on application No. 10-1999-067746 and No. 10-2000-82085 filed in the Korean Industrial Property Office on Dec. 31, 1999 and Dec. 26, 2000 respectively, the content of which is incorporated hereinto by reference.

BACKGROUND OF THE INVENTION (a) Field of the Invention

The present invention relates to an electronic device, and particularly to an electronic device comprising an organic compound having p-type semiconductor characteristics and performing functions of injecting or transporting holes.

(b) Description of the Related Art

Organic compounds having p-type semiconductor characteristics, which has conductance in-between insulating material and conducting material, has been widely applied to OPC drums (organic photo conductor drum) and used in a copying press or a laser printer, etc. Specifically, aryl amine-type material forms a thin film on the drum of a laser printer as a blend with polymers such as polycarbonate to constitute a hole-transporting layer. For such an application, organic compounds having p-type semiconductor characteristics must have appropriate hole-mobility, and electrical, thermal and morphological stability for hole.

Devices using the p-type organic semiconductors are largely classified into the following two groups.

The first group has an application in an OPC drum or a solar cell or a photovoltaic cell. Specifically, an outer light-source is introduced into devices to generate exiton, and the exiton is separated into electrons and holes. At this time, the p-type organic semiconductor performs the function of transporting the separated holes in devices.

The second group applies voltage to two or more electrodes to directly inject a carrier into an organic semiconductor that constitute an interface with the electrode. As examples, devices such as an organic EL (electroluminescence) that injects electrons and holes respectively and simultaneously from two electrodes and emits light, devices such as transistor that transports a carrier from a source to a drain by voltage applied to a gate to perform a function of switching, etc. can be mentioned. At this time, it is important to form a stabilized interface between the p-type organic semiconductor substances and the electrodes. Generally, since an electrode consists of metallic substances or metal oxides, the performances of devices can be significantly decreased due to an electric field applied to devices or heat applied from the outside or generated from the inside unless the interface between inorganic substances and organic substances is stabilized.

The above-mentioned arylamine-type compounds have been widely used as semiconductor substances comprising organic substances showing p-type characteristics, and oligothiophene or polythiophene are also known to show high carrier mobility when experimentally used in the manufacture of thin film transistor.

Such characteristics of the compounds allow a variety of applications thereof. Specifically, arylamine type p-type organic semiconductor used in an OPC drum is also applied to an organic light-emitting diode, and oligothiophene used in a thin film transistor is also used as a hole-injecting or hole-transporting material of an organic light-emitting diode. In addition, an organic solar cell, which uses a hole-transporting material of solid state, also employs arylamine type derivatives that are used as a hole-transporting material of an organic light-emitting diode (Adv. Mater. 12, 447, 2000). Such compatibility suggests that any organic substances having p-type semiconductor characteristics can be widely used in the manufacture of devices considering their energy levels, hole-transporting capabilities, environments, etc.

The p-type organic semiconductor used in an organic light-emitting diode performs the function of facilitating hole-injection from an anode and simultaneously transporting the injected hole to a light-emitting layer. At this time, the layer may be separated into two layers of hole-injecting layer and hole-transporting layer. In order to secure the stability of devices, substances should be selected from those capable of constituting stable interface with an anode comprising metal or metal oxide. In addition, in order to facilitate hole injection thereby enabling low voltage operation of devices, the substances should have appropriate oxidation potential and high capability of transporting the injected holes.

In order to satisfy these requirements, U.S. Pat. No. 4,356,429 discloses copper phthalocyanine and U.S. Pat. No. 5,540,999 discloses oligothiophene. In addition, quinacridone type materials disclosed in U.S. Pat. No. 5,616,427 are also known to contribute to the stability of devices.

Recently, the stability of polymeric light-emitting diode has been largely improved by separately introducing a hole-transporting layer between an anode comprising metal oxide and a light-emitting material. Particularly in thermally stable polymeric light-emitting diode, substance that is inserted between an anode and a light-emitting polymer to stabilize an interface despite high glass transition temperature and that facilitates the injection of holes can largely improve performances, particularly life and operating voltage of devices (J. Appl. Phys. 84, 6859, 1998).

The p-type organic semiconductor, when used as hole-injecting material, exhibits an effect of preventing device short of light-emitting diode that may be generated during a manufacturing process of devices, as well as an effect of prolonging life of devices. Generally, organic light-emitting diode having organic substance thickness of 100 to 200 nm may become device short due to pinholes that can be generated during organic substance deposition or at the unstable interface between anode and organic substances. At this time, the injection of stable hole-injecting layer can decrease the possibility of such devices short, and particularly the injection of thick hole-injecting layer can largely decrease such possibility.

However, in the common case where the hole-injecting material has semiconductor characteristics instead of conducting characteristics, adverse effects of increasing operating voltage may be shown according to the thickness of hole-injecting material.

SUMMARY OF THE INVENTION

The present invention is made in consideration of the problems of the prior art, and it is an object of the present invention to provide an electronic device comprising a layer of organic compounds that can transport or inject holes, decrease operation voltage, and improve life of devices.

It is another object of the present invention to provide an electronic device comprising a layer of organic compounds that can form a stable interface with an electrode.

BRIEF DESCRIPTION OF THE DRAWINGS

A more complete appreciation of the invention, and many of the attendant advantages thereof, will be readily apparent as the same becomes better understood by reference to the following detailed description when considered in conjunction with the accompanying drawings, wherein.

DETAILED DESCRIPTION AND THE PREFERRED EMBODIMENTS

Figure 1:
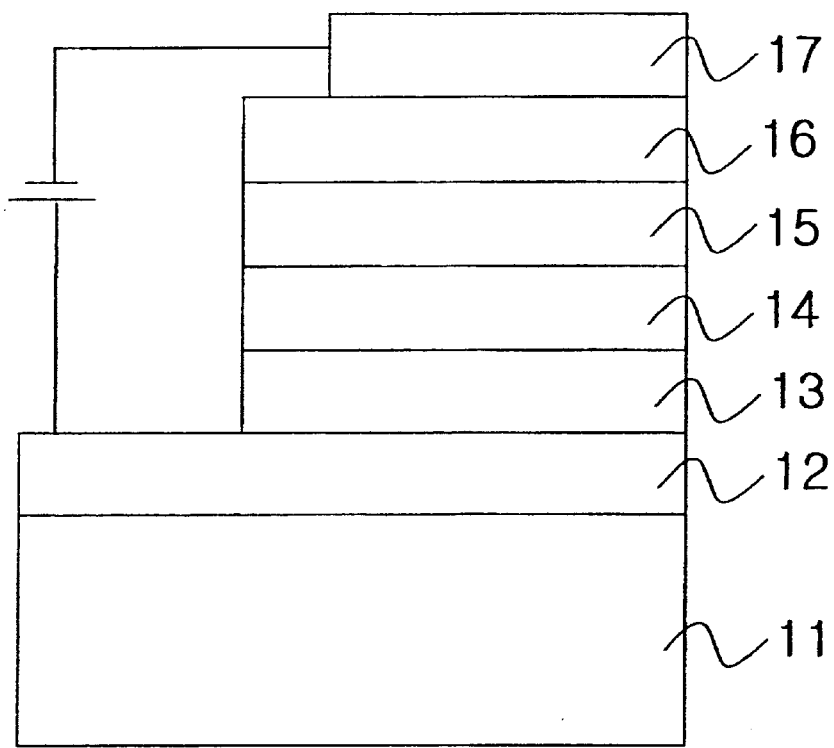
FIG. 1 is a simplified cross-sectional view of an organic light-emitting diode according to an example of the present invention.

In the following detailed description, only the preferred embodiment of the invention has been shown and described, simply by way of illustration of the best mode contemplated by the inventors of carrying out the invention. As will be realized, the invention is capable of modification in various obvious respects, all without departing from the invention. Accordingly, the drawings and description are to be regarded as illustrative in nature, and not restrictive.

In order to achieve the above objects, the present invention provides an organic light-emitting diode in which at least one or more layers comprising an organic compound represented by the following Chemical Formula 1 are interposed between an anode and a cathode:

[Chemical Formula 1]

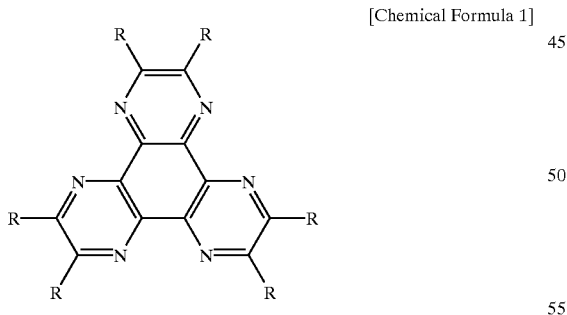

Wherein, each R is independently or simultaneously selected from the group consisting of hydrogen atom, C1–12 hydrocarbon, halogen, alkoxy, arylamine, ester, amide, aromatic hydrocarbon, heterocyclic compound, nitro, and nitrile (—CN) group.

The layer comprising the organic compound represented by the Chemical Formula 1 is preferably a hole-injecting layer, a hole-transporting layer or a hole-injecting and transporting layer.

The present invention also provides an electronic device comprising thin film layers, said device comprising at least one of a hole-injecting layer, a hole-transporting layer and a hole-injecting and transporting layer comprising the organic compound represented by the Chemical Formula 1.

The present invention will now be explained in more detail.

First, the compound represented by the Chemical Formula 1 used in the electronic device of the present invention will be explained.

It is disclosed in U.S. Pat. No. 4,780,536 that the compound of the Chemical Formula 1 can be used as a cross-linking agent of heat resistance polymers, and it has been predicted that the compound can be used as an n-type organic semiconductor that transports electrons in electronic device based on organic substance owing to its low reduction potential (Polymer Preprint 40, 404, 1999). Particularly, it is known that the compound of the Chemical Formula 1, when each R is nitrile group, has a reduction potential of only 0.01 V and thus it clearly has n-type organic semiconductor characteristics.

The present inventors have discovered that the organic compound of the Chemical Formula 1 is a p-type organic semiconductor contrary to the prediction of the prior art that it may be an n-type organic semiconductor, and employs it as a hole-injecting, hole-transporting, or hole-injecting and transporting material in electronic devices such as organic light-emitting diode, etc., thereby decreasing the operation voltage of electronic devices and improving the life of devices. In addition, since the compound has a capability of forming a stable interface with metal oxides, it can be applied to various electronic devices.

The representative examples of the compound of the Chemical Formula 1 of the present invention include those represented by the following Chemical Formulae 1a, 1b, 1c and 1d.

[Chemical Formula 1a]

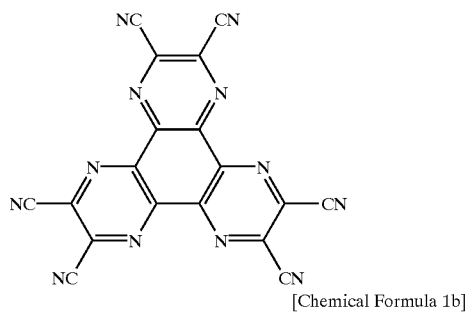

[Chemical Formula 1b]

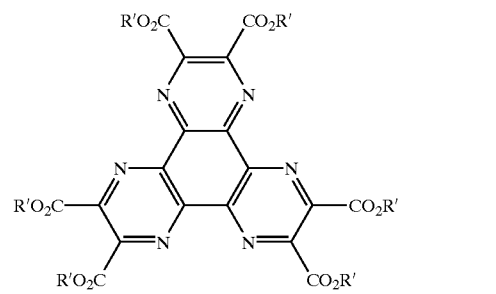

-continued

[Chemical Formula 1c]

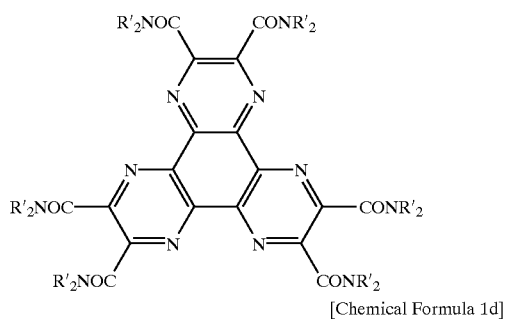

[Chemical Formula 1d]

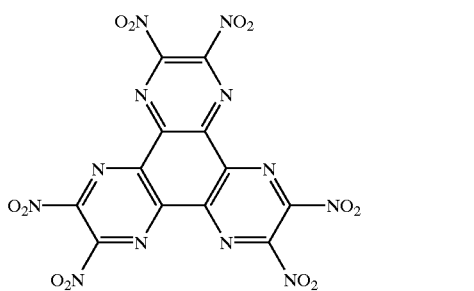

Wherein, each substituent of ester and amide represented by R' of the compound of the Chemical Formula 1b and 1c is independently or simultaneously selected from hydrogen, C1–15 hydrocarbon, phenyl, other aromatic groups, etc., and C3–15 higher hydrocarbon having high flexibility is preferable when a thin film is formed by spin-coating.

The organic light-emitting diode is an electronic device having a multi-layered structure of thin films.

The organic light-emitting diode of the present invention comprises at least one organic substance layer in the form of thin film interposed between an anode and a cathode, which constitutes a hole-injecting layer that receives holes from an anode, or performs a function of transporting holes to a light-emitting layer or transporting holes simultaneously by injecting them.

Figure 2:
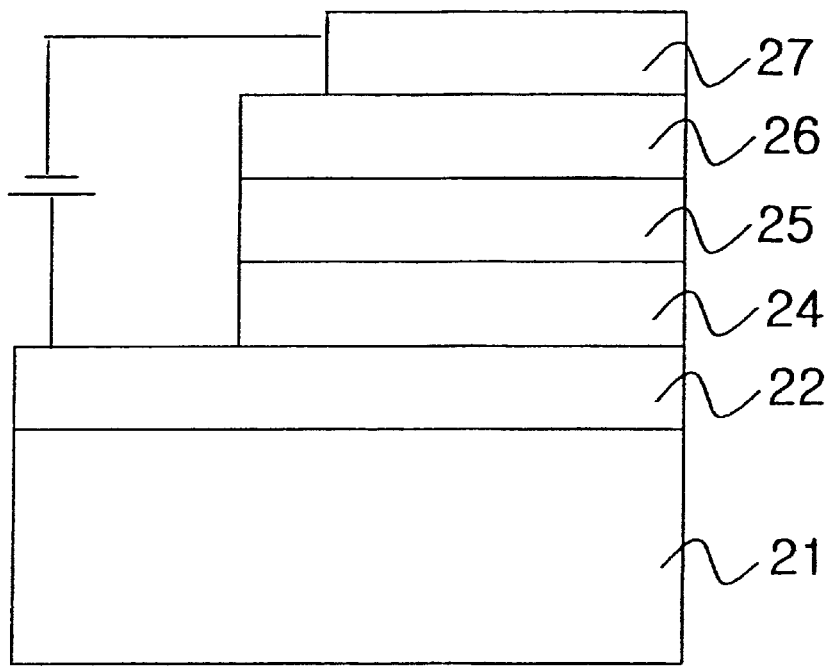
FIG. 2 is a simplified cross-sectional view of an organic light-emitting diode having different structure according to the another example of the present invention.

The general structure of organic light-emitting diode consists of multi-layers as shown in FIG. 1, in which e.g., an indium tin oxide thin film is coated on a transparent substrate (11) to form a transparent electrode, i.e., an anode (12), on which a hole-injecting layer (13), a hole-transporting layer (14), a light-emitting layer (15), an electron-transporting layer (16) and a cathode layer (17) are sequentially laminated. Alternatively, as shown in FIG. 2, it may have a structure consisting of a transparent substrate (21), a transparent electrode (22), a layer simultaneously performing hole-injection and transportation (24), a light-emitting layer (25), an electron-transportation layer (26) and a cathode layer (27).

If necessary, the device may have more or less number of multi-layers, and may have a plurality of light-emitting layer. The hole-injecting layer, hole-transporting layer or hole-injecting and transporting layer containing the compound of the Chemical Formula 1 can form a plurality of layers corresponding to the structure of the device and can be variously applied.

As the transparent substrate (11, 21), glass or plastics of amorphous properties can be preferably used, and substrates having appropriate mechanical strength and surface flatness such as metal or wafer can be used according to the use.

In addition, as a transparent electrode, metal oxides or oxides of mixed metals such as tin oxide, indium tin oxide, zinc oxide, indium zinc oxide, etc. can be used, and metals having high work function such as gold, or conductive polymers in which appropriate dopants are added to polymers such as PEDOR (poly[3,4-(ethylene-1,2-dioxy)thiophene], polyaniline, polypyrrole, polythiophene, etc., can be used.

As material forming the hole-injecting layer (13) in FIG. 1, the compound represented by the Chemical Formula 1 can be used alone or in combination with other kinds of hole-injecting materials. As examples of other hole-injecting materials used together with the compound of the Chemical Formula 1, p-type organic semiconductors such as copper phthanlocyanine or oligothiophene, etc. can be mentioned. When other materials are used together, the organic compound of the Chemical Formula 1 can be used in an amount of 1 wt % to 100 wt %. In addition, the thickness of the layer is preferably 0.1 to 10,000 nm, and more preferably 10 to 300 nm.

When other kinds of hole-injecting materials, i.e., p-type organic semiconductors are used together with the compound of the Chemical Formula 1, the amount of injected holes can be controlled according to the ratio of a mixture. Specifically, when the material has different energy level and different mobility for holes, the kind and ratio of mixture that can control the concentration of holes most suitably to the construction of devices can be examined.

As a result of studies, it has been found that when the organic compound of the Chemical Formula 1 is used as the hole-injecting layer, an operation voltage does not significantly increase despite of the change in thickness of hole-transporting layer from 10 to 200 nm, contrary to copper phthalocyanine. Consequently, the possibility of generating device short can be decreased and an operation voltage can be lowered by using a hole-injecting layer as a back film of a hole-transporting layer.

When the organic compound of the Chemical Formula 1 forms the hole-injecting layer (13) and it is not used as a hole-transporting layer (14), the hole-transporting layer can be separately formed with conventional arylamine type compounds or polycyclic aromatic compounds. As examples of the hole-transporting material, 4,4'-bis[N-(1-naphtyl)-N-phenyl-amino]biphenyl (NPB) can be mentioned, and other kinds of hole-transporting material can be used in order to optimize the ratio of injected electrons and holes. In addition, the organic compound of the Chemical Formula 1 performs a function of smoothly injecting holes from an anode and directly transporting them to a light-emitting layer, when it forms a hole-injecting and transporting layer (24), as shown in FIG. 2.

The light-emitting layer (15, 25) of the organic light-emitting diode according to the present invention, where electrons and holes injected from two opposite electrodes are recombined and emit light, employs materials having high fluorescence efficiency. As representative examples, 8-hydroxyquinoline aluminum salt (Alq3), dimerized styryl compound described in U.S. Pat. No. 5,366,811, benzoxazole derivatives and a metal complex thereof, benzimidazole derivatives and a metal complex thereof, and polymers such as poly(p-phenylene vinylene)) and derivatives thereof or copolymer derivatives, polyfluorene and derivatives thereof., etc. can be mentioned.

The electron-transporting layer (16, 26) in FIGS. 1 and 2, which receives electrons from a cathode (17, 27) and transports them to a light-emitting layer, employs material that smoothly injects electrons from a cathode and simultaneously forms a stable interface with the cathode. The light-emitting layer (15, 25) may be used as a layer that emits light and simultaneously transports electrons without a separate electron-transporting layer. As representative examples of electron-transporting material, Alq3 is most commonly used and copper phthalocyanine can be used. In addition, in order to effect light-emission in dyes, the material of light-emitting layer in FIG. 2 must be similar to or smaller than those forming a host of light-emitting layer that dops material capable of transporting holes such as arylamine compounds with fluorescent dye and causes light-emission in dyes. As representative examples of fluorescent dyes, rubrene, etc. can be mentioned. As material forming a cathode, material having low work function is used so as to easily inject electrons into an electron-transporting layer. As examples, alloys such as lithium-aluminum alloy, magnesium-silver alloy, etc., magnesium, calcium, etc. can be used. In addition, an electrode having two-layered structure of e.g., LiF/aluminium and $Li_2O$/aluminium can be used. In addition, the injection of electrons can be facilitated and the interface between electrode and electron-transporting layer can be fortified by mix-depositing the electron-transporting layer and electrode.

The compound of the Chemical Formula 1 can be applied to an organic thin film transistor using p-type organic semiconductors, a photocoltaic cell, an OPC of laser printer or a cloying press, etc., as well as to the organic light-emitting diode. Particularly, the compound of the Chemical Formula 1 is suitable for a p-type organic thin film transistor, since the organic thin film transistor must form a stable interface with a fate insulator and rapidly transport holes from a source to a drain.

The present invention is described in detail through the following EXAMPLES and COMPARATIVE EXAMPLES. However, these EXAMPLES are for illustrating the present invention and not for limiting the present invention.

EXAMPLE

Example 1

To confirm the effect that the compound satisfying Chemical Formula 1 brings down the drive-voltage of an organic light-emitting device, the following organic light-emitting device was manufactured, using the compound of Chemical Formula 1a satisfying Chemical Formula 1 as a hole-injecting material.

A glass substrate coated with a thin film of ITO (indium tin oxide) having thickness of 1500 Å was ultrasonically cleaned in a solution comprising a cleaning agent, dried, and transferred into a plasma cleaning device. The substrate was cleaned with oxygen plasma for 5 minutes, and transferred to a vacuum vapor deposition device.

Figure 3:
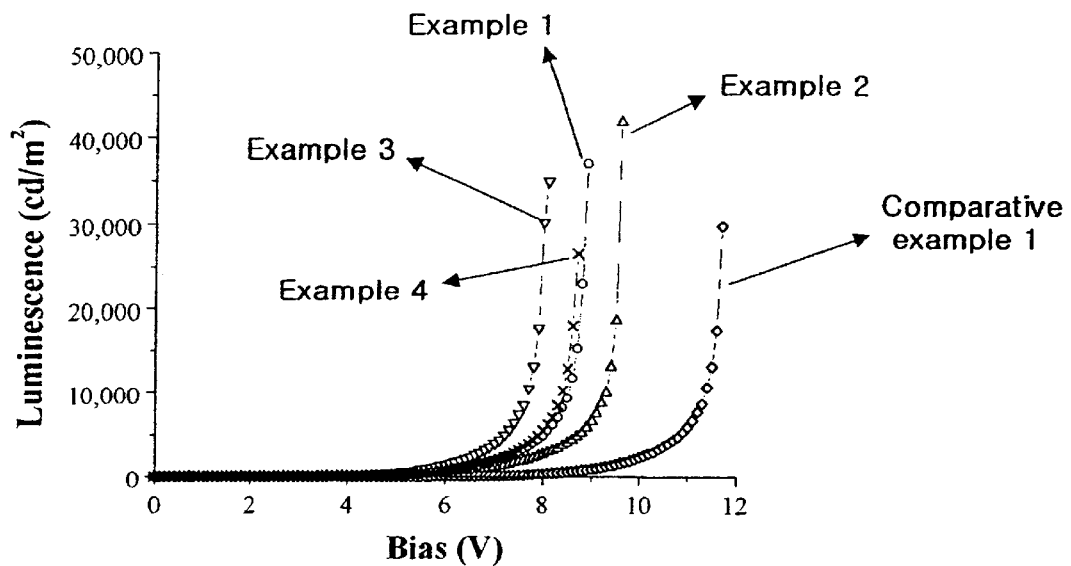
FIG. 3 is a graph showing the correlation between brightness and the voltage of the organic light-emitting diode of the present invention.

A hole-injecting layer having thickness of 200 Å was formed by thermal vacuum depositing the compound of Chemical Formula 1a satisfying Chemical Formula 1 over the conductive substrate. NPB (600 Å) as a hole-transporting material and Alq3(600 Å) having both of electron-transporting and light-emitting properties was deposited on the substrate in order. Then, an electrode was formed by depositing 5 Å of LiF and 2500 Å of aluminum on the electron-transporting layer. In the process, the deposing speed was maintained by 1 Å/sec for organic material, 0.2 Å/sec for lithium fluoride, and 3~7 Å/sec for aluminum. FIG. 3 illustrates voltage-brightness relationship for the manufactured organic light-emitting device.

Example 2

An organic light-emitting device was manufactured by using the same process of Example 1, wherein the thickness of Chemical Formula 1a as a hole-injecting layer was increased by 1000 Å instead of 200 Å. FIG. 3 illustrates voltage-brightness relationship for the manufactured organic light-emitting device.

Example 3

To prove that when the hole-injecting layer would be formed by using a mixture the compound of Chemical Formula 1a satisfying Chemical Formula 1 and the other stable material to holes, it showed low drive-voltage characteristics, the following device was manufactured, and its characteristics was measured.

An organic light-emitting device was manufactured using by the same process of Example 1, wherein mixture having thickness of 500 Å composed of 90 weight % of Chemical Formula 1a and 10 weight % of copper phthalocyanine complex used instead of Chemical Formula 1a thickness of 200 Å as a hole-injecting layer by co-evaporation method. FIG. 3 illustrates voltage-brightness relationship for the manufactured organic light-emitting device.

Example 4

To prove that when the hole-injecting layer would be formed by using a mixture the compound of Chemical Formula 1a satisfying Chemical Formula 1 and the other stable material to holes, it showed low drive-voltage characteristics and could improve a light-emitting life, the following device was manufactured, and its characteristics was measured.

An organic light-emitting device was manufactured by using the same process of Example 1, wherein mixture having thickness of 500 Å composed of 70 weight % of Chemical Formula 1a and 30 weight % of copper phthalocyanine complex used instead of Chemical Formula 1a thickness of 200 Å as a hole-injecting layer by co-evaporation method FIG. 3 illustrates voltage-brightness relationship for the manufactured organic light-emitting device. Measuring a half-life of brightness for the device was carried out in the direct current density of 100 mA/cm$^2$, and a half-life of brightness was 180 hours.

Comparative Example 1

To prove that the compound of Chemical Formula 1a satisfying Chemical Formula 1 has lower drive-voltage characteristics than the conventional hole-injecting layer, the most universally known copper phthalocyanine complex was used, and the most universally used thickness was used as below.

An organic light-emitting device was manufactured using by the same process of Example 1, wherein hole-injecting layer was formed by deposing copper phthalocyanine complex having thickness of 150 Å instead of Chemical Formula 1a. FIG. 3 illustrates voltage-brightness relationship for the manufactured organic light-emitting device. Measuring a half-life of brightness for the device was carried out in the direct current density of 100 mA/cm$^2$, and a half-life of brightness was 93 hours.

Example 5

To measure ability that the compound of Chemical Formula 1a satisfying Chemical Formula 1 has injected and transported holes, voltage-current relationship was obtained by while applying a forward bias to the thin film manufactured by deposing the material of Chemical Formula 1a. At this point, ITO was used in anode, and aluminum having high work function was used in cathode. This device was manufactured by the following method.

Figure 4:
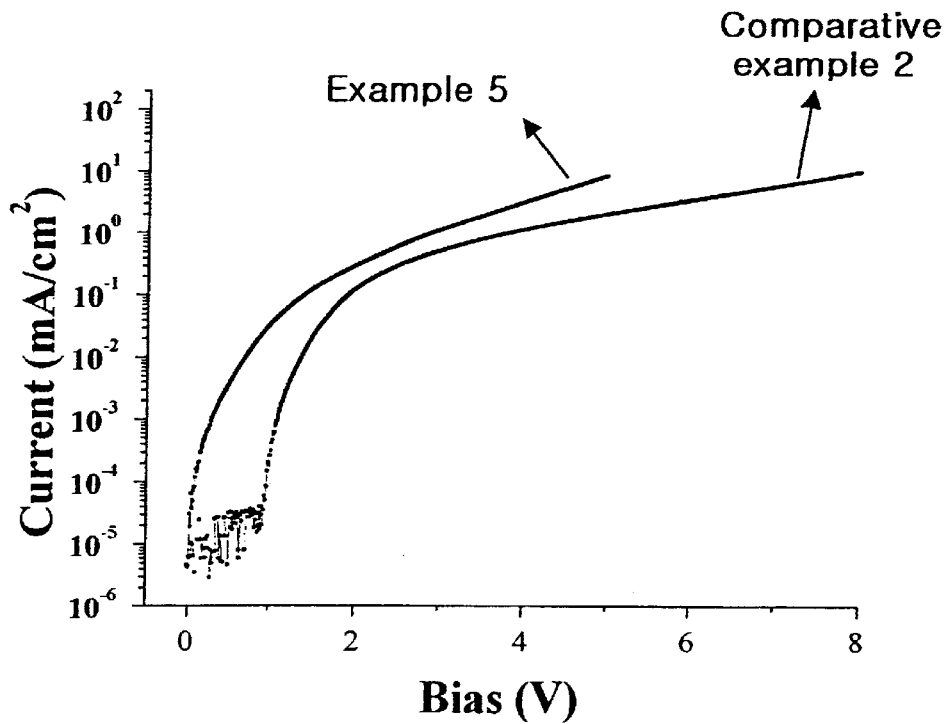
FIG. 4 is a graph showing the correlation between a current density and a voltage of device manufactured in order to examine p-type semiconductor characteristics of the substance used in the present invention Reference numerals (11) and (21) indicates a transparent substrate, (12) and (22) an anode, (13) a hole-injecting layer, (14) a hole-transporting layer, (15) and (25) a light-emitting layer, (16) and (26) an electron-transporting layer, (17) and (27) a cathode layer, and (24) a hole-injecting and transporting layer.

A glass substrate coated with a thin film of ITO (indium tin oxide) having thickness of 1500 Å was ultrasonically cleaned in an solution comprising a cleaning agent, dried, and transferred into a plasma cleaning device. The substrate was cleaned with oxygen plasma for 5 minutes, and transferred to a vacuum vapor deposition device. A hole-injecting layer having thickness of 2000 Å was formed by thermal vacuum depositing the compound of Chemical Formula 1a satisfying Chemical Formula 1 over the substrate. Cathode was formed on the layer by deposing Aluminum having thickness of 2500 Å. In the process, the deposing speed was maintained by 1 Å/sec for organic material, and 3~7 Å/sec for aluminum. In the voltage-current relationship for the manufactured organic light-emitting device as shown in FIG. 4, the device using the compound of Chemical Formula 2 injected holes as soon as 0 volt was over, the concentration of holes always was higher than the device using NPB as shown in Comparative Example 2. As disclosed above, it proves that hole-injecting of the material of Chemical Formula 1a is easier than the widely known p-type organic semiconductor material, and its ability of hole-transporting is superior.

Comparative Example 2

To compare with ability of hole-injecting and hole-transporting for the compound of Chemical Formula 1a, the added voltage-the injected current (hole) relationship was obtained by applying arylamine based NPB to the device which has been a p-type organic semiconductor widely used in hole-transporting material of organic light-emitting device and OPC drum as the same method of Example 7.

A glass substrate coated with a thin film of ITO (indium tin oxide) having thickness of 1500 Å was ultrasonically cleaned in an solution comprising a cleaning agent, dried, and transferred into a plasma cleaning device. The substrate was cleaned with oxygen plasma for 5 minutes, and transferred to a vacuum vapor deposition device. A hole-injecting layer having thickness of 1600 Å was formed by thermal vacuum depositing NPB over the substrate. Cathode was formed on the layer by deposing Aluminum having thickness of 2500 Å. In the process, the deposing speed was maintained by 1 Å/sec for organic material, and 3~7 Å/sec for aluminum. FIG. 4 illustrates voltage-current relationship for the manufactured device.

In the voltage-current relationship for the manufactured organic light-emitting device as shown in FIG. 4, the device using NPB injected holes at about 1 volt, the concentration of holes was lower than the device using the compound of Chemical Formula 1a.

As shown in Examples and Comparative Examples, the compound of Chemical Formula 1a that is one of examples satisfying Chemical Formula 1 has p-type organic semiconductor characteristics, when it used in a hole-injecting layer acquired of p-type semiconductor characteristics, it can make use low drive-voltage in an organic light-emitting device, and when it mixed with other appropriate material, it can make maintain low drive-voltage according with the relative ratio.

Furthermore, it discovered that a half-life of the device has been more stable than copper phthalocyanine complex that could be maintain stable conventionally. This phenomenon shows that the compound of Chemical Formula 1 of the present invention has superior hole-injecting ability, and superior hole-transporting ability, and can be formed stable interface with the electrodes.

Therefore it shows that the compound has other device application that acquired of hole-injection or hole-transporting characteristics.

The devices of this invention can improve a light-emitting life greatly, and can has low drive-voltage because of comprising layer having an organic compound of p-type semiconductor characteristics.

While the present invention has been described in detail with reference to the preferred embodiments, those skilled in the art will appreciate that various modifications and substitutions can be made thereto without departing from the spirit and scope of the present invention as set forth in the appended claims.

What is claimed is:

1. An organic light-emitting device comprising at least one or more layers interposed between an anode and a cathode, wherein the one or more layers comprise an organic compound represented by Chemical Formula 1:

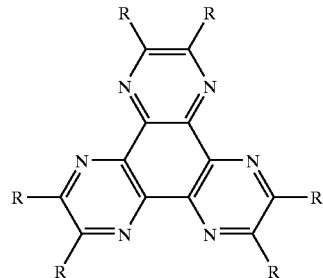

(Chemical Formula 1)

wherein, each R is independently or simultaneously selected from the group consisting of hydrogen atom, $C_1$–$C_{12}$ hydrocarbon, halogen, alkoxy, arylamine, ester, amide, aromatic hydrocarbon, heterocyclic compound, nitro, and nitrile (—CN) group, and wherein the organic compound represented by the Chemical Formula 1 is a p-type organic semiconductor.

2. The organic light-emitting device as defined in claim 1, wherein the layer comprising the organic compound represented by the Chemical Formula 1 is a hole-injecting layer, a hole-transporting layer, or a hole-injecting-and-transporting layer.

3. The organic light-emitting device as defined in claim 1, wherein the device comprises in order:
   a) a transparent substrate;
   b) an anode;
   c) a hole-injecting layer;
   d) a hole-transporting layer;
   e) a light-emitting layer;
   f) an electron-transporting layer; and
   g) a cathode.

4. The organic light-emitting device as defined in claim 1, wherein the device comprises in order:
   a) a transparent substrate;
   b) an anode;
   c) a hole-injecting-and-transporting layer;
   d) a light-emitting layer;
   e) an electron-transporting layer; and
   f) a cathode.

5. The organic light-emitting device as defined in claim 1, wherein the compound of the Chemical Formula 1 is represented by Chemical Formula 1a:

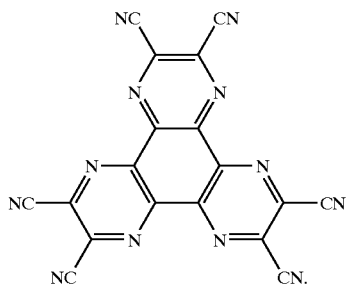

(Chemical Formula 1a)

6. The organic light-emitting device as defined in claim 1, wherein the compound of the Chemical Formula 1 is represented by Chemical Formula 1b:

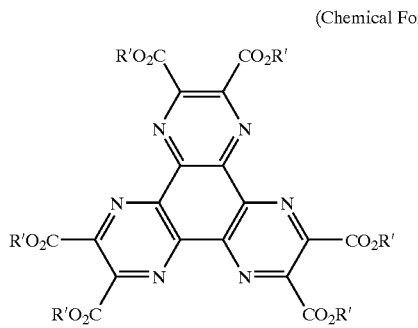

(Chemical Formula 1b)

wherein each R' is independently or simultaneously, hydrocarbon having 1~15 carbon atoms, phenyl, or aromatic group.

7. The organic light-emitting device as defined in claim 1, wherein the compound of the Chemical Formula 1 is represented by Chemical Formula 1c:

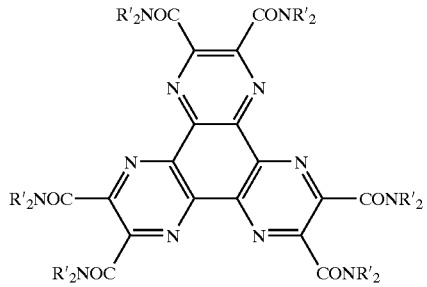

(Chemical Formula 1c)

wherein each R' is independently or simultaneously, hydrocarbon having 1~15 carbon atoms, phenyl, or aromatic group.

8. The organic light-emitting device as defined in claim 1, wherein the compound of the Chemical Formula 1 is represented by Chemical Formula 1d:

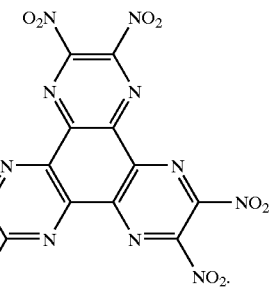

(Chemical Formula 1d)

9. The organic light-emitting device as defined in claim 1, wherein the thickness of the layer comprising the organic compound represented by the Chemical Formula 1 is 10~10,000 nm.

10. The organic light-emitting device as defined in claim 1, wherein the layer comprising the organic compound represented by the Chemical Formula 1 further comprises a hole-injecting material selected from the group of copper phthalocyanine complex, arylamine based compound, and polycyclic aromatic compound.

11. The organic light-emitting device as defined in claim 1, wherein the anode comprises a conducting polymer, or a conducting metal oxide.

12. The organic light-emitting device as defined in claim 1, wherein the compound represented by the Chemical Formula 1 has the capability of forming a stable interface with metal oxides.

13. The organic light-emitting device as defined in claim 1, wherein the organic compound represented by the Chemical Formula 1 is a light-emitting diode.

14. The organic light-emitting device as defined in claim 13, comprising at least one organic substance layer in the form of thin film interposed between an anode and a cathode, which constitutes a hole-injecting layer that receives holes from an anode, or performs a function of transporting holes to a light-emitting layer or transporting holes simultaneously by injecting them.

15. The organic light-emitting device as defined in claim 13, consisting of multi-layers, in which an indium tin oxide thin film is coated on a transparent substrate to form a transparent anode, on which a hole-injecting layer, a hole-transporting layer, a light-emitting layer, an electron-transporting layer and a cathode layer are sequentially laminated.

16. The organic light-emitting device as defined in claim 13, consisting of a transparent substrate, a transparent anode, a layer simultaneously performing hole-injection and transportation, a light-emitting layer, an electron-transportation layer and a cathode layer.

17. A process for preparing the organic light-emitting device as defined in claim 1 comprising sequentially forming on a transparent substrate the anode, on the anode the p-type organic semiconductor represented by the Chemical Formula 1, on the p-type organic semiconductor a light-emitting layer, on the light-emitting layer an electron-transporting layer and on the electron-transporting layer the cathode.

18. The process as defined in claim 17, wherein the p-type organic semiconductor forms a hole-injecting layer, a hole-transporting layer, or a hole-injecting-and-transporting layer.

19. A process for preparing the organic light-emitting device as defined in claim 1 comprising sequentially forming on a transparent substrate the anode, a light-emitting layer, and the cathode, wherein the organic compound represented by the Chemical Formula 1 as defined in claim 1 is deposited between the anode and the light-emitting layer, and wherein the organic compound represented by the Chemical Formula 1 is the p-type organic semiconductor.

20. The process as defined in claim 19 wherein the organic compound represented by Chemical Formula 1 forms a hole-injecting layer, a hole-transporting layer or a hole-injecting-and-transporting layer.

21. The organic light-emitting device as defined in claim 2, wherein the device consists essentially of:
    a) a transparent substrate;
    b) the anode on the transparent substrate;
    c) the hole-injecting layer on the anode, wherein the hole-injecting layer consists essentially of one or more of the organic compounds represented by the Chemical Formula 1 and optionally one or more of the compounds selected from the group consisting of: arylamine compounds, 4,4'-bis[N-(1-naphtyl)-N-phenyl-amino]biphenyl, copper phthalocyanine complexes, and polycyclic aromatic compounds;
    d) the hole-transporting layer on the hole-injecting layer, wherein the hole-transporting layer consists essentially of one or more of the compounds selected from the group consisting of: the organic compounds represented by the Chemical Formula 1, arylamine compounds, 4,4'-bis[N-(1-naphtyl)-N-phenyl-amino]biphenyl, and polycyclic aromatic compounds;
    e) a light-emitting layer on the hole-transporting layer, wherein the light-emitting layer consists essentially of one or more compounds selected from the group consisting of: 8-hydroxyquinoline aluminum salt, dimerized styryl compounds, benzoxazole derivatives and metal complexes thereof, benzimidazole derivatives and metal complexes thereof, poly(p-phenylene vinylene) and derivatives thereof, copolymer derivatives of poly(p-phenylene vinylene), and polyfluorene and derivatives thereof;
    f) an electron-transporting layer on the light-emitting layer; and
    g) the cathode on the electron-transporting layer.

22. The organic light-emitting device as defined in claim 21, wherein the electron-transporting layer consists essentially of one or more of the compounds selected from the group consisting of: 8-hydroxyquinoline aluminum salt and copper phthalocyanine.

23. The organic light-emitting device as defined in claim 2, wherein the device consists essentially of:
    a) a transparent substrate;
    b) the anode on the transparent substrate;
    c) the hole-injecting-and-transporting layer on the anode, wherein the hole-injecting-and-transporting layer consists essentially of one or more of the organic compounds represented by the Chemical Formula 1 and optionally one or more of the compounds selected from the group consisting of: arylamine compounds, 4,4'-bis[N-(1-naphtyl)-N-phenyl-amino]biphenyl, and copper phthalocyanine complex, polycyclic aromatic compounds;
    d) a light-emitting layer on the hole-injecting-and-transporting layer, wherein the light-emitting layer consists essentially of one or more compounds selected from the group consisting of: 8-hydroxyquinoline aluminum salt, dimerized styryl compounds, benzoxazole derivatives and metal complexes thereof, benzimidazole derivatives and metal complexes thereof, poly(p-phenylene vinylene) and derivatives thereof, copolymer derivatives of poly(p-phenylene vinylene), and polyfluorene and derivatives thereof;
    e) an electron-transporting layer on the light-emitting layer; and
    f) the cathode on the electron-transporting layer.

24. The organic light-emitting device as defined in claim 23, wherein the electron-transporting layer consists essentially of one or more of the compounds selected from the group consisting of: 8-hydroxyquinoline aluminum salt and copper phthalocyanine.

25. The organic light-emitting device as defined in claim 2, wherein the device consists essentially of:
    a) a transparent substrate;
    b) the anode on the transparent substrate;
    c) the hole-injecting layer on the anode, wherein the hole-injecting layer consists essentially of one or more of the organic compounds represented by the Chemical Formula 1 and optionally one or more of the compounds selected from the group consisting of: arylamine compounds, 4,4'-bis[N-(1-naphtyl)-N-phenyl-amino]biphenyl, copper phthalocyanine complexes, and polycyclic aromatic compounds;
    d) the hole-transporting layer on the hole-injecting layer, wherein the hole-transporting layer consists essentially of one or more of the compounds selected from the group consisting of: the organic compounds represented by the Chemical Formula 1, arylamine compounds, 4,4'-bis[N-(1-naphtyl)-N-phenyl-amino] biphenyl, and polycyclic aromatic compounds;
    e) a light-emitting layer on the hole-transporting layer, wherein the light-emitting layer consists essentially of one or more compounds selected from the group consisting of: 8-hydroxyquinoline aluminum salt, dimerized styryl compounds, benzoxazole compounds and metal complexes thereof, benzimidazole compounds and metal complexes thereof, poly(p-phenylene vinylene), copolymers of poly(p-phenylene vinylene), and polyfluorene;
    f) an electron-transporting layer on the light-emitting layer; and
    g) the cathode on the electron-transporting layer.

26. The organic light-emitting device as defined in claim 25, wherein the electron-transporting layer consists essentially of one or more of the compounds selected from the group consisting of: 8-hydroxyquinoline aluminum salt and copper phthalocyanine.

27. The organic light-emitting device as defined in claim 2, wherein the device consists essentially of:
    a) a transparent substrate;
    b) the anode on the transparent substrate;
    c) the hole-injecting-and-transporting layer on the anode, wherein the hole-injecting-and-transporting layer consists essentially of one or more of the organic compounds represented by the Chemical Formula 1 and optionally one or more of the compounds selected from the group consisting of: arylamine compounds, 4,4'-bis [N-(1-naphtyl)-N-phenyl-amino]biphenyl, and copper phthalocyanine complexes, polycyclic aromatic compounds;
    d) a light-emitting layer on the hole-injecting-and-transporting layer, wherein the light-emitting layer consists essentially of one or more compounds selected from the group consisting of: 8-hydroxyquinoline aluminum salt, dimerized styryl compounds, benzoxazole compounds and metal complexes thereof, benzimidazole compounds and metal complexes thereof, poly(p-phenylene vinylene), copolymers of poly(p-phenylene vinylene), and polyfluorene;

e) an electron-transporting layer on the light-emitting layer; and f) the cathode on the electron-transporting layer.

28. The organic light-emitting device as defined in claim 27, wherein the electron-transporting layer consists essentially of one or more of the compounds selected from the group consisting of: 8-hydroxyquinoline aluminum salt and copper phthalocyanine.

29. An electronic device comprising at least one or more layers selected from a group consisting of a hole-injecting layer, a hole-transporting layer, and a hole-injecting-and-transporting layer, wherein the one or more layers comprise an organic compound represented by the Chemical Formula 1:

(Chemical Formula 1)

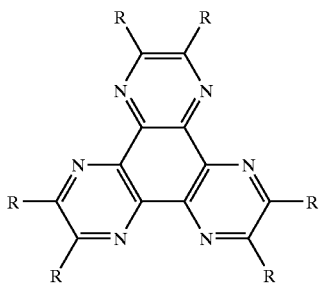

wherein, each R is independently or simultaneously selected from the group consisting of hydrogen atom, $C_1$–$C_{12}$ hydrocarbon, halogen, alkoxy, arylamine, ester, amide, aromatic hydrocarbon, heterocyclic compound, nitro, and nitrile (—CN) group, and wherein the organic compound represented by Chemical Formula 1 is a p-type organic semiconductor.

30. The electronic device as defined in claim 29, wherein the device is an organic thin film based transistor, a photo voltaic cell, or an organic photo conductor based drum.

31. A p-type organic semiconductor represented by the Chemical Formula 1:

(Chemical Formula 1)

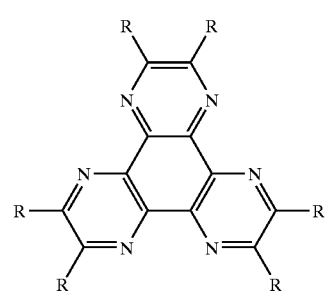

wherein, each R is independently or simultaneously selected from the group consisting of hydrogen atom, $C_1$–$C_{12}$ hydrocarbon, halogen, alkoxy, arylamine, ester, amide, aromatic hydrocarbon, heterocyclic compound, nitro, and nitrile (—CN) group.

* * * * *